(12) United States Patent
Smith et al.

(10) Patent No.: US 9,034,517 B1
(45) Date of Patent: May 19, 2015

(54) CAPACITORS HAVING CONDITIONED CARBON FOR ELECTRODES

(71) Applicant: Retriev Technologies Incorporated, Anaheim, CA (US)

(72) Inventors: W. Novis Smith, Philadelphia, PA (US); Joel McCloskey, Philadelphia, PA (US)

(73) Assignee: RETRIEV TECHNOLOGIES INCORPORATED, Anaheim, CA (US)

( * ) Notice: Subject to any disclaimer, the term of this patent is extended or adjusted under 35 U.S.C. 154(b) by 0 days.

(21) Appl. No.: 14/073,302

(22) Filed: Nov. 6, 2013

(51) Int. Cl.
*H01M 8/04* (2006.01)
*H01G 11/62* (2013.01)
*H01M 10/056* (2010.01)

(52) U.S. Cl.
CPC ............. *H01G 11/62* (2013.01); *H01M 10/056* (2013.01)

(58) Field of Classification Search
CPC .................... H01M 10/0525; H01M 10/0569; H01M 10/0568; H01M 10/056; H01M 2300/0025; H01M 4/131; H01M 4/133; Y02E 60/13
USPC ............ 429/212, 218.1, 220; 252/500, 521.5, 252/521.6
See application file for complete search history.

(56) References Cited

U.S. PATENT DOCUMENTS

| | | | |
|---|---|---|---|
| 4,892,944 A | 1/1990 | Mori et al. | |
| 5,260,855 A | 11/1993 | Kaschmitter et al. | |
| 5,969,936 A * | 10/1999 | Kawasato et al. | 361/502 |
| 6,535,373 B1 | 3/2003 | Smith et al. | |
| 6,743,947 B1 | 6/2004 | Xu et al. | |
| 6,902,683 B1 | 6/2005 | Kaji et al. | |
| 6,980,415 B2 | 12/2005 | Higono et al. | |
| 7,436,651 B2 | 10/2008 | Takeda et al. | |
| 7,656,645 B2 | 2/2010 | Chiba | |
| 7,722,989 B2 | 5/2010 | Ohzuku et al. | |
| 7,924,549 B1 | 4/2011 | Smith et al. | |
| 7,939,200 B2 | 5/2011 | Ohzuku et al. | |
| 8,007,938 B2 | 8/2011 | Kotato et al. | |
| 8,043,745 B2 | 10/2011 | Kotato et al. | |
| 8,435,681 B2 | 5/2013 | Yamada et al. | |
| 2006/0024577 A1 | 2/2006 | Schwake | |
| 2007/0002522 A1 | 1/2007 | Takeda et al. | |
| 2007/0194266 A1 | 8/2007 | Chiba | |
| 2007/0224514 A1 | 9/2007 | Kotato et al. | |
| 2008/0318135 A1 * | 12/2008 | Sung et al. | 429/339 |
| 2010/0021819 A1 * | 1/2010 | Zhamu et al. | 429/231.8 |
| 2011/0300453 A1 * | 12/2011 | Kotato et al. | 429/330 |
| 2012/0244426 A1 | 9/2012 | Kotato et al. | |
| 2013/0095379 A1 | 4/2013 | Kotato et al. | |
| 2013/0196225 A1 | 8/2013 | Kotato et al. | |

FOREIGN PATENT DOCUMENTS

| | | |
|---|---|---|
| CN | 101096339 A | 1/2008 |
| JP | 2000228216 A | 8/2000 |
| JP | 2007 273395 A | 10/2007 |

OTHER PUBLICATIONS

Organikum. Praktikum po organicheskoi khimii II. Perevod s nemetskogo, Izdatelstvo "Mir", Moskva, 1979, pp. 76, 78-79 (See Written Opinion for relevance).

Notification of Transmittal Of The International Search Report and The Written Opinion of the International Searching Authority, or the Declaration Issued for Application No. PCT/US 2014/064276 Dated Feb. 5, 2015.

Gu G.Y. et al.; *2-Methoxyethyl (methyl) Carbonate-Based Electrolytes for Li-ion Batteries*; Electrochimica Acta, 2000, 45, pp. 3127-3139, Abstract Tables 2, 6.

Notification of Transmittal Of The International Search Report and The Written Opinion of the International Searching Authority, or the Declaration Issued for Application No. PCT/US 2014/064275 Dated Jan. 29, 2015.

* cited by examiner

*Primary Examiner* — Cynthia H Kelly
*Assistant Examiner* — Monique Wills
(74) *Attorney, Agent, or Firm* — RatnerPrestia

(57) ABSTRACT

There is provided an improvement for capacitors having activated carbon electrodes by the use of an electrolyte solution containing a carbonate of the formula $RO(C{=}O)OR^1$ and a conductive salt such as a lithium salt or a quaternary ammonium salt at a concentration of from 0.6 to 3 mol/l.

13 Claims, No Drawings

CAPACITORS HAVING CONDITIONED CARBON FOR ELECTRODES

FIELD OF THE INVENTION

The present invention relates to novel electrolyte solutions for electrochemical devices such as capacitors and having carbon electrodes with conditioned carbon elements. More particularly, there is a synergism found with the use of the electrolyte solutions with the conditioned carbon cathodes which improves the energy density with a conductive salt such as a lithium salt or quaternary ammonium salt.

BACKGROUND OF THE INVENTION

The performance of ultra capacitor and lithium batteries electrolytes at low temperature is a continuing problem since the conductivity of the electrolyte will go to zero if it freezes before a desired low temperature performance is achieved. Various blends of organic carbonates have been used along with the addition of ethers and low molecular weight esters to achieve low temperature (−60° C.) freezing points of the mixed solvents containing lithium hexafluorophosphate for low temperature lithium-ion battery performance. The use of mixtures of ethylmethyl carbonate with dimethyl carbonate and small quantities of ethylene carbonate have allowed performance down to −20° C. and even −30° C. in some cases for lithium battery electrolytes. The use of tetrahydrofuran (THF) and methyl formate and methyl acetate and dimethyl ethylene glycol (glyme) or dimethoxy ethane (DME) has allowed some battery electrolytes to achieve −40° C. or even −50° C. performance. The problem is that the performance of these electrolytes at high temperature such as >70° C. causes high vapor pressures in the batteries with these volatile low boiling solvents. In the case of ultra capacitors based on organic electrolytes the situation is similar except most current ultra capacitor electrolytes are based on the use of acetonitrile (low boiling with by 82° C.) containing tetraethylammonium tetrafluoroborate. These ultra capacitor electrolytes have an upper operating voltage limitation of 2.7 V. The use of capacitor electrolyte solvents based on the organic carbonates and containing tetraalkylammonium tetrafluoroborates has also been limited because of solubility limitations when using propylene carbonate, or by low temperature performance when using mixtures containing ethylene carbonate.

Propylene carbonate has been used in mixtures with other organic carbonates for capacitor electrolytes but this solvent also limits cell voltage to about 3 V and the solubility of the tetrafluoroborate salt decreases rapidly on cooling and results in low conductivity of the electrolyte at temperatures below −20° C. The use of ethylene carbonate (mp 35° C.) with cyclic organic carbonate mixtures containing organic quaternary tetrafluoroborate salts for capacitor use gives higher operating cell voltage in ultra capacitors, but these electrolytes freeze before −20° C. is reached. Low temperature cycling performance (non-freezing) is desired (required for the use of ultra capacitor performance in vehicle performance down to −30° C.). In aircraft, the temperature desired is down to −40° C. At the same time these applications desire high temperature performance (>70° C.) with low vapor pressure. This means that volatile solvents which are used for low temperature performance cause problems at the high end of the desired performance range.

Activated carbon is the preferred material for use in preparing electrodes for carbon electrode capacitors. This activated carbon is prepared from a number of different sources such as coconut shells, wood, sugar, cellulosics and phenolic resins. After converting these materials to carbon under steam controlled conditions, the carbons are "activated" in a second step using steam or catalyzed with KOH, NaOH and/or carbon dioxide and KOH to increase the surface area to very high surface areas such as 1000 to 2400 $m^2/g$. These activated carbons usually contain about 2% oxygen after they have been thoroughly dried and traces of inorganic salts. This oxygen is probably present as quinones, hydroquinones, esters, phenols, carboxylic acids, furans and possibly ketones etc. with some nitrogen compounds present—all of which under high voltage conditions greater than 3 V. will undergo electrochemical oxidation/reduction as the voltage is increased past 3.3 V. At lower voltages, these functional groups actually improve the energy storage capacity of the carbon and are desirable at voltages below 3.2 V.

The basic components of electrical capacitors include conductive electrodes connected to an electric power supply and a dielectric material separating the electrodes. Electrolytic capacitors and electrochemical double layer capacitors also have an electrolyte. In an electrolyte capacitor, the electrodes are provided by an oxide or carbon layer formed on metal foil and are separated by a porous non-conducting membrane such as paper, porous polymer, etc. The liquid electrolyte provides electrical contact to the opposite electrode through the separator. The inherently high resistance of electrolytic capacitors is generally mitigated by rolling a large sheet of the electrode material into a roll to give high surface area. In an electrochemical double layer capacitor, the dielectric is provided by the electrolyte. In this type of capacitor the resistance of the electrolyte is a significant factor in the total device resistance. In capacitors that use electrolytes, the temperature has a major influence on the electrolyte in the performance of the capacitor since the conductivity of the electrolyte decreases with temperature.

Electrochemical double layer capacitors including super capacitors, typically comprise electrodes, electrical contacts to a power supply, separators for electrodes and/or cells, and electrolyte and environmental seals. As mentioned above, a key component of electrolytic and electrochemical double layer capacitors is the electrolyte, which typically comprises a combination of a conductive salt and a solvent. Desirable electrolytes are typically liquid with low viscosity, low density, and high conductivity over a range of ambient temperature conditions. They should also be commercially inexpensive, chemically and electrochemically stable, and compatible with carbon. Aqueous electrolyte systems have been used extensively and provide voltage restricted below 1.8 V. For example, ultra capacitors in Japan are not permitted to use acetonitrile for the electrolyte. A need exists for improved electrolyte systems that provide optimum capacitance for capacitors to achieve high power density, a wide temperature range, and a long lifetime without memory effects.

The key requirements for the electrolyte in both non-aqueous batteries and capacitors are high voltage stability, low temperature performance and electrochemical stability. U.S. Pat. No. 6,743,947 to Xu, et al. discloses an electrolyte system comprising a mixture of ethylene carbonate and dimethyl carbonate at a concentration of the electrolyte salt at 0.5–2.5 M which has poor conductivity at low temperatures.

U.S. Pat. No. 7,924,549 to Smith, et al discloses conditioned carbon electrodes for capacitors and lithium batteries having conditioned carbon electrodes that have also been heat treated and used in an electrolyte comprising a quaternary ammonium tetrafluoroborate salt in an aprotic solvent.

U.S. Patent Application Publication No. 20070002522 discloses capacitors having electrodes with alkali-activated carbon electrodes in electrolytic solutions comprising a quaternary ammonium salt and a solvent containing a carboxylic ester.

Electrochemical double layer capacitors capable of high energy density, known as "super-capacitors", have been assembled from a variety of materials. In general, it is desirable to construct super-capacitors with light weight materials and electrolytes that are stable and non-reactive, as described in U.S. Pat. No. 5,260,855 issued to Kaschmitter et al., the teachings of which are hereby incorporated by reference. This type of super-capacitor incorporates electrodes based on carbon that may be prepared from organic gels.

U.S. Pat. No. 6,902,683 to Smith et al., which is herein incorporated by reference, relates to electrolytes of a complex salt formed by mixing of a tetraalkyl ammonium salt of hydrogen fluoride with an imidazolium compound in a nitrile solvent which operate at temperatures between −60 and 150 degrees C.

The article of Ue in J. Electrochem. Soc. Vol 141, No. 11, November 1994 entitled "Electrochemical Properties of Organic Liquid Electrolytes Based on Quaternary Onium Salts for Electrical Double-Layer Capacitors" which is herein incorporated by reference, discloses high permittivity solvents and onium salts for double-layer capacitors. Specifically studied were quaternary onium tetrafluoroborate salts which showed greater solubility in the solvents with good stability and conductivity.

U.S. Pat. No. 6,980,415 to Higono et al, which is herein incorporated by reference, discloses an electrolyte for capacitors comprising dimethyl carbonate and a spiro tetrafluoroborate salt. The tetrafluoroborate salt can be used in the present invention with the present electrolyte solutions.

SUMMARY OF THE INVENTION

According to one embodiment of the invention, there is provided lithium ion batteries and capacitors containing carbon electrodes, an electrolyte solution which comprises a conductive salt such as a lithium salt or a quaternary ammonium salt and a solvent system comprised of at least 20% by weight (i.e., 25 to 75% by weight) of one or more symmetrical and unsymmetrical (asymmetrical) carbonates of the formula:

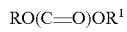

wherein R is selected from the group consisting of methyl, ethyl, propyl, isopropyl, $CH_3OCH_2CH_2$—, $CH_3OCH_2CH_2OCH_2CH_2$—, $CH_3OCH_2CH_2OCH_2CH_2OCH_2CH_2$—, R"$OCH_2CH_2$— and R"—O—$(CH_2)_n$—, n is 2, 3 or 4, $R^1$ is selected from the group consisting of $CH_3OCH_2CH_2$—, $CH_3OCH_2CH_2OCH_2CH_2$—, $CH_3OCH_2CH_2OCH_2CH_2OCH_2CH_2$—, $CH_3CH_2OCH_2CH_2$— and R"—O—$CH_2CH_2$—, and R" is methyl, ethyl, propyl or isopropyl.

According to another embodiment of the invention, the novel carbonates of the invention can be mixed with each other or with other organic cyclic or linear carbonates, ethers and carboxylic esters such that they comprise at least 20% by weight of the solvent systems. For example, the solvent system employed in the electrolyte solution may be comprised of 20 to 100% by weight of a carbonate, or a combination of carbonates, meeting the aforementioned formula RO(C=O)OR$^1$, with the balance of the solvent system being one or more solvents selected from the group consisting of cyclic carbonates, linear carbonates not having the formula RO(C=O)OR$^1$, ethers, carboxylic esters, and combinations thereof.

According to an embodiment of the invention, the solvents are utilized in combination with capacitors having carbon electrodes which have been "activated" or post-treated to remove all chemically bound oxygen, nitrogen and sulfur and preferably heat treated after acid washing at temperatures of 1100-1500° C. under an inert atmosphere. Preferably, the surface area of the carbon present in the carbon electrode is >1200 m$^2$/g.

In another embodiment of the invention, the internal resistance of the ultra capacitor cells is reduced or minimized by lowering the functional Equivalent Series Resistance (ESR) as measured on the RCL meter (Resistance Capacitance and Inductance) which measures the capacitor's impedance in a circuit. The lower the ESR the faster at which the capacitor can be charged and discharged. The ESR limits the power at which the device can operate from a direct or alternating current.

The term "capacitors" as used herein refers to all capacitors which are provided with at least one activated carbon electrode and include Electric Double Layer Capacitors (EDLC) and Ultra Capacitors (UC).

It is a yet still further object of the invention to provide an ultra capacitor having a stable operating cell voltage of about 4V when containing, as part of an electrolyte solution, about 2M of a quaternary ammonium tetrafluoroborate salt at room temperature.

DESCRIPTION OF THE PREFERRED EMBODIMENTS

According to the present invention there is provided capacitors having the synergistic combination of at least one activated carbon electrode in an electrolyte solution comprising a conductive salt (e.g., a lithium salt or a quaternary ammonium salt) in a concentration of 0.6 to 3 M wherein the solvent system used for the electrolyte solution is acetonitrile free and comprises 20 to 100% by weight, preferably 25 to 75% by weight, of one or more symmetrical and/or unsymmetrical carbonates of the formula:

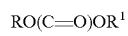

wherein R is selected from the group consisting of methyl, ethyl, isopropyl, propyl, $CH_3OCH_2CH_2$—, $CH_3OCH_2CH_2OCH_2CH_2$—, $CH_3OCH_2CH_2OCH_2CH_2OCH_2CH_2$—, R"$OCH_2CH_2$— and R"—O—$(CH_2)_n$—, n is 2, 3 or 4, $R^1$ is selected from the group consisting of $CH_3OCH_2CH_2$—, $CH_3OCH_2CH_2OCH_2CH_2$—, $CH_3OCH_2CH_2OCH_2CH_2OCH_2CH_2$—, $CH_3CH_2OCH_2CH_2$— and R"—O—$CH_2CH_2$—, and R" is methyl, ethyl, propyl or isopropyl.

According to another embodiment of the invention the carbonate solvents of the invention may be a mixture of themselves or with other linear or cyclic carbonates, esters and/or ethers, preferably ethylene carbonate.

Cyclic carbonates include ethylene carbonate (hereafter designated as EC) and propylene carbonate (PC). Linear carbonates include dimethyl carbonate (DMC), diethyl carbonate (DEC), ethylmethyl carbonate (EMC), etc.

The carboxylic ester used herein preferably has three or more carbon atoms and one or more carboxylic ester bonds. The upper limit of the number of carbon atoms in the carboxylic ester is not particularly limited. In view of the compatibility with the linear carbonate and/or cyclic carbonate, the carboxylic ester preferably has ten or less carbon atoms and more preferably eight or less carbon atoms.

The number of carboxylic ester bonds in the carboxylic ester is one or more as described above. Since an increase in the number of carboxylic ester bonds generally leads to an increase in the viscosity of the carboxylic ester, the number of carboxylic ester bonds is preferably one or two.

Examples of suitable carboxylic esters include dimethyl succinate, ethyl methyl succinate, diethyl succinate, dimethyl 2-methylsuccinate, ethyl methyl 2-methylsuccinate, dimethyl glutarate, ethyl methyl glutarate, diethyl glutarate, dimethyl 2-methylglutarate, ethyl methyl 2-methylglutarate, diethyl 2-methylglutarate, dimethyl adipate, ethyl methyl adipate, diethyl adipate, 1,2-diacetoxyethane, 1,2-diacetoxypropane, 1,4-diacetoxybutane, glycerin triacetate, methyl 4-acetoxybutyrate, gamma butyrolactone, and methyl 2-acetoxyisobutyrate, ethyl acetate and methyl acetate.

The electrolyte solutions of the present invention for capacitors comprise the solvent systems of the invention and at least one conductive salt dissolved as an electrolyte.

The conductive salt may be any that is capable of being used in electrical storage devices, such as lithium secondary cells, lithium ion secondary cells and electrical double-layer capacitors. Conductive salts that may be used include alkali metal salts and quaternary ammonium salts. Combinations and mixtures of different conductive salts may be utilized.

Preferred alkali metal salts are lithium salts, sodium salts and potassium salts. Specific examples include: (1) lithium salts such as lithium tetrafluoroborate, lithium hexafluorophosphate, lithium perchlorate, lithium trifluoromethanesulfonate, sulfonyl imide lithium salts, sulfonyl methide lithium salts, lithium acetate, lithium trifluoroacetate, lithium benzoate, lithium p-toluenesulfonate, lithium nitrate, lithium bromide, lithium iodide and lithium tetraphenylborate; (2) sodium salts such as sodium perchlorate, sodium iodide, sodium tetrafluoroborate, sodium hexafluorophosphate, sodium trifluoromethanesulfonate and sodium bromide; and (3) potassium salts such as potassium iodide, potassium tetrafluoroborate, potassium hexafluorophosphate and potassium trifluoromethanesulfonate.

Highly conductive quaternary ammonium and related imidazolium salts and triflates and mixtures thereof as tetrafluoroborates have synergistic effect on their solubilities and conductivities at low temperatures when dissolved in the solvent systems of the invention.

Preferable specific examples of the quaternary ammonium salt useful in the present invention include, but are not limited to, triethylmethylammonium tetrafluoroborate, diethyldimethylammonium tetrafluoroborate, ethyltrimethylammonium tetrafluoroborate, dimethylpyrrolidinium tetrafluoroborate, diethylpyrrolidinium tetrafluoroborate, ethylmethylpyrrolidinium tetrafluoroborate, spiro-(1,1$^1$)-bipyrrolidinium tetrafluoroborate, dimethylpiperidinium tetrafluoroborate, diethyl piperidinium tetrafluoroborate, spiro-(1,1$^1$)-bipiperidinium tetrafluoroborate, piperidine-1-spiro-1$^1$-pyrrolidinium tetrafluoroborate, and the triflates thereof. The quaternary ammonium tetrafluoroborate salts preferably have a molecular weight in the range of 178-240.

Of these, triethylmethylammonium tetrafluoroborate, spiro-(1,1$^1$)-bipyrrolidinium tetrafluoroborate, diethyl pyrrolidinium tetrafluoroborate, dimethylpyrrolidinium tetrafluoroborate, and the like are particularly preferable.

The concentration of the conductive salt in the electrolytic solution of the present invention is preferably from 0.6 to 3 mol/l, particularly preferably from 1 M to 2 M of the electrolytic solution.

If the concentration of the conductive salt is less than 0.6 mol/l, the conductivity may be insufficient; if more than 3 mol/l, the low temperature performance and economical efficiency may be impaired.

What is needed are solvents with high operating voltages greater than 3 V for the ultra capacitor in which conductive salts are very soluble and which have a wide liquidus range, preferably from −70° C. to >150° C. In addition, the electrolyte solution should remain liquid with high salt concentrations of salt, e.g., from >1 M up to 2 M. The organic carbonates of the invention meet all of these requirements. The preferred solvent is methyl methoxyethyl carbonate ($CH_3O(C=O)OCH_2CH_2OCH_3$), (MMC). The liquidus range of this solvent is about −65° C. to 170° C., providing outstanding low temperature and high temperature performance while dissolving a high level of conductive salt. This solvent has a stable operating cell voltage of about 4 V in ultra capacitor performance when containing 2 M diethyldimethyl ammonium tetrafluoroborate at room temperature. Other quaternary alkylammonium tetrafluoroborates can also be used for this same stable high operating voltage in this solvent and related solvents. This same stable solvent with 2 M quaternary ammonium tetrafluoroborate salt will reversibly charge/discharge cycle at −45° C. in an ultra capacitor.

Preparation of Novel Carbonate Solvents

A direct synthesis for the symmetrical and asymmetrical members of the family of organic carbonates is the following equilibration:

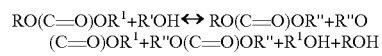

(in the presence of basic catalyst such as sodium methoxide)

In the case of dimethyl carbonate and 2-methoxy ethanol this becomes:

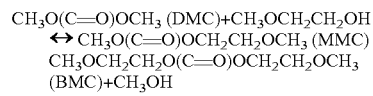

After equilibration, the catalyst can be neutralized with an acid or acid salt and the reaction mixture distilled to remove the alcohols and obtain pure organic carbonate components or a useful mixture of organic carbonates. Using an excess of the DMC in this case favors more of the desired MMC (asymmetrical component) as opposed to the symmetrical component bis-2-methoxyethyl carbonate (BMC). Mixtures of both with the starting material can be used as long as the alcohols are removed. The MMC is a preferred solvent of these series of organic carbonates. MMC may be isolated in pure form by distillation.

Preparation of Preferred Carbon Electrodes

The preferred carbon electrodes of the invention can be prepared following the procedure disclosed in U.S. Pat. No. 7,924,549 of Smith, et al., incorporated herein by reference in its entirety for all purposes.

The capacitor requires two electrodes. Electrodes may be made of 90% treated carbon and 10% Kynar® binder in an acetone slurry. A 1-mil thick sheet of aluminum foil pretreated with a conductive carbon layer may be trimmed to size and prepared for coating. A draw knife may be used to deliver the proper thickness of slurry coating onto the foil. Once coated onto the treated aluminum sheet, the acetone evaporates and then the other side of the aluminum foil may be coated. Once the second side has been coated, proper sized rectangles may be cut from the aluminum sheet with small plain aluminum tabs still attached to one end. Once cut, the electrodes may be baked under vacuum to remove any residual moisture.

Once removed from the baking/vacuum treatment small squares of Surlyn® resin sheets may be welded to the small plain aluminum tabs. This allows for future secure welding to the assembled flexible foil pouch.

To improve the functioning components in order to increase the performance of the ultra capacitor (UC) at higher voltage, we have been able to have stable cycling at 3.9-4.0 V with selected electrolytes and carbons. An additional aspect for better performance is to minimize the internal resistance of the UC, which depends on the measured ESR of the cell. It was found that one can lower the functional ESR of our UC cells by heat treating at higher temperatures the activated carbons used in the cells. It was found that with cleaned carbons under inert atmosphere one can continue to gain improvement by going from 1100° C. up to 1300° C. However, while going up to about 1400° C. may offer further reduction in ESR the effect did not appear to be different than 1300° C., and the surface area (capacity) appeared to start being affected negatively. Therefore, the range of post heat treatment after acid washing of the carbon is 1100° C. to 1500° C., with the preferred range being 1250-1300° C. under inert atmosphere.

The ESR of cells was reduced as follows:

| Peak Temperature (2 hrs) of treated carbon | ESR-ohms | mAH Capacity at 3.9 V |
| --- | --- | --- |
| 1100° C. | 0.4 | 3.0 to 3.5 |
| 1200° C. | 0.3 | 3.4 to 3.7 |
| 1250° C. | 0.2 | 3.6 to 3.8 |
| 1300° C. | 0.18 | 3.8 to 4.0 |

Part of the reason for this improvement is the improvement of carbon conductivity which occurs significantly in going from 1000° C. to about 1400° C. and then only very slowly increases after that with increases in temperature. At the same time a high surface area carbon such as an activated carbon begins to rearrange and collapses to a more graphitic nature, thus losing its high surface area which is needed for the performance of the ultra capacitor. This surface collapse increases more and rapidly as the temperature is increased starting at about 1200° C. and proceeding more rapidly as the temperature is raised past 1400° C. Empirically, it was found that this optimum heating range to achieve maximum conductivity before degradation of the surface area is harmful to be about 1250° C. to 1300° C. for two hours with purified activated carbons. In addition to improving the conductivity while preserving the surface area, the higher temperature (above 1100° C.) chemically eliminates most (if not all) chemically bound oxygen and nitrogen, which are susceptible to electrochemical oxidation reduction at cell voltages above approximately 3.4 V in the ultra capacitor. Their presence contributes to leakage current (electrochemical oxidation currents on charging the UC and accelerate self discharge) which degrades UC performance, especially at operating voltages above 3.4V.

It is understood that conditioning the carbon electrodes according to the present preferred process optimizes the performance of the ultra capacitor when used with the electrolyte solutions of the invention, the prior art carbon electrodes, for example, which have been alkali conditioned will also be synergistically improved with the electrolyte solutions of the invention.

Example 1

Preparation of Electrolyte Solvent

In a 2 L 3-necked flask, 1749 g (21.9 moles) of dimethyl-carbonate (DMC), 246.14 g (3.24 moles) of 2-methoxy ethanol, and 49.23 g (5 wt. %) of a 25% sodium methoxide in methanol solution were added. A 250° C. thermometer was added to the flask and the reaction flask was then fitted to a distillation apparatus containing a thermometer and a collection flask. This was stirred at room temperature for 30 minutes until a cloudy, white suspension began to form. The mixture was then heated slowly to a reaction flask temperature of 73° C. At this point, the first drop of distillate was collected at 43° C. The distillate was continuously collected and checked by GC for the presence of products (MMC and bis(2-methoxy ethyl)-carbonate (BMC)). This was continued until the reaction flask reached a temperature of 100° C. and the distillation temperature reached 72° C. At this point, the reaction flask contents contained only a small percentage of DMC and no methanol. The reaction mixture was allowed to cool to room temperature. The reaction mixture was then filtered to remove the sodium methoxide catalyst. The slightly yellow filtrate was treated with NaH$_2$PO$_4$, mixed, and re-filtered. This step was then repeated and the filtrate checked to assure that no catalyst remained. The filtrate was then transferred to a 500 mL 3-necked flask and stirred. This was then vacuum-distilled slowly. The first fraction started at a distillation temperature of 28° C. and a reaction flask temperature of 35° C. These fractions were mostly DMC. The MMC laden fractions were collected under vacuum (24 mm Hg) at a distillation temperature of 43° C. and a reaction flask temperature of 55° C. The GC analysis showed a 91% yield of MMC in the final fraction of MMC product collected. The remainder of the mix was composed of 6% BMC and 3% 2-methoxy ethanol.

What is claimed is:

1. An electrochemical device comprising the combination of a conditioned and heat treated carbon electrode comprised of a metal collector and a layer comprised of activated carbon formed on the metal collector, wherein the activated carbon has been heated after acid washing at a temperature of 1100° C. to 1500° C. under an inert atmosphere and consists essentially of carbon, and an electrolyte solution, the electrolyte solution comprising a non-aqueous solvent system comprising 20 to 100% by weight of one or more symmetrical and/or asymmetrical carbonates of the general formula:

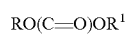

RO(C=O)OR$^1$ wherein R is selected from the group consisting of methyl, ethyl, isopropyl, propyl, CH$_3$OCH$_2$CH$_2$—, CH$_3$OCH$_2$CH$_2$OCH$_2$CH$_2$—, CH$_3$OCH$_2$CH$_2$OCH$_2$CH$_2$OCH$_2$CH$_2$—, R"OCH$_2$CH$_2$— and R"—O—(CH$_2$)$_n$—, n is 2, 3 or 4, R$^1$ is selected from the group consisting of CH$_3$OCH$_2$CH$_2$—, CH$_3$OCH$_2$CH$_2$OCH$_2$CH$_2$—, CH$_3$OCH$_2$CH$_2$OCH$_2$CH$_2$OCH$_2$CH$_2$—, CH$_3$CH$_2$OCH$_2$CH$_2$— and R"—O—CH$_2$CH$_2$—, and R" is methyl, ethyl, propyl or isopropyl, and a conductive salt which is selected from the group consisting of quaternary ammonium tetrafluoroborates and quaternary ammonium triflates at a concentration of from 0.6 to 3 mol/l.

2. The electrochemical device of claim 1 wherein the non-aqueous solvent system is comprised of at least 20% by weight methyl-(2-methoxyethyl)-carbonate.

3. The electrochemical device of claim 1 wherein the non-aqueous solvent system is comprised of at least 20% by weight bis(2-methoxyethyl) carbonate.

4. The electrochemical device of claim 1 wherein the activated carbon of the carbon electrode has a surface area greater than 1200 m$^2$/g.

5. The electrochemical device of claim 1 wherein the conductive salt is selected from the group consisting of tetraethyl ammonium tetrafluoroborate, triethylmethylammonium tetrafluoroborate, diethyldimethylammonium tetrafluoroborate, ethyltrimethylammonium tetrafluoroborate, dimethylpyrrolidinium tetrafluoroborate, diethylpyrrolidinium tetrafluoroborate, ethylmethylpyrrolidinium tetrafluoroborate, and spiro-(1,1¹)-bipiperidinium tetrafluoroborate, piperidine-1-spiro-1¹-pyrrolidinium tetrafluoroborate and the triflates thereof.

6. The electrochemical device of claim 1 wherein the carbon after heat treatment has a surface area greater than 1200 m²/g.

7. The electrochemical device of claim 1 wherein the non-aqueous solvent system includes a solvent selected from the group consisting of dimethyl carbonate, ethyl methyl carbonate, ethylene carbonate, propylene carbonate and diethyl carbonate.

8. The electrochemical device of claim 1 wherein the electrochemical device is an ultra capacitor.

9. The electrochemical device of claim 1 wherein the electrochemical device is an electrochemical double layer capacitor.

10. The electrochemical device of claim 1 wherein the electrolyte solution has a liquidus range from −70° C. to greater than 150° C.

11. The electrochemical device of claim 1 wherein the non-aqueous solvent system consists of asymmetric methyl-(2-methoxy ethyl)-carbonate.

12. The electrochemical device of claim 1, wherein the non-aqueous solvent system is comprised of 25 to 75% by weight of one or more symmetrical and/or asymmetrical carbonates of the general formula:

$$RO(C=O)OR^1$$

13. The electrochemical device of claim 12, wherein the non-aqueous solvent system is additionally comprised of ethylene carbonate.

* * * * *